United States Patent [19]
White

[11] 3,957,819
[45] May 18, 1976

[54] 2-(HALO ALKYLAMINO)-3-PHENYL-3H-INDOLE-3-OLS

[75] Inventor: Alan Chapman White, Windsor, England

[73] Assignee: John Wyeth & Brother Limited, Maidenhead, England

[22] Filed: Dec. 9, 1974

[21] Appl. No.: 531,019

[30] Foreign Application Priority Data
Dec. 20, 1973 United Kingdom............... 59065/73

[52] U.S. Cl.................. 260/326.15; 260/251 A; 260/325 R; 424/251; 424/274
[51] Int. Cl.².............. C07D 209/34; C07D 239/00
[58] Field of Search............................... 260/326.15

[56] References Cited
UNITED STATES PATENTS
3,577,435  5/1971  Bell et al.................... 260/326.15

OTHER PUBLICATIONS
Meyer et al., Chem. Abstracts, Vol. 70, p. 259, No. 11468 e, (1969).

Primary Examiner—Lewis Gotts
Assistant Examiner—S. P. Williams
Attorney, Agent, or Firm—David E. Frankhouser

[57] ABSTRACT

The invention relates to indole derivatives of the formula

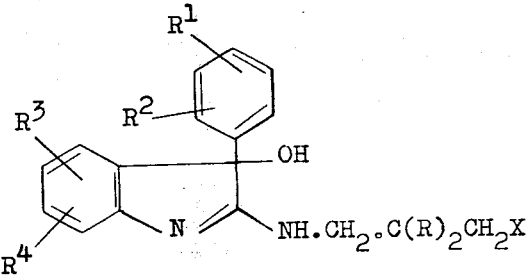

and their acid addition salts wherein R is hydrogen or lower alkyl, $R^1$, $R^2$, $R^3$ and $R^4$ are each hydrogen, hydroxyl, lower alkyl, lower alkoxy, trifluoromethyl or halogen and X is a halogen atom. The compounds are useful as antidepressant agents. They can also be cyclised to form anti-depressant 10-aryl-2,3,4,10-tetrahydropyrimido-[1,2-a]indol-10-ols.

4 Claims, No Drawings

2-(HALOALKYLAMINO)-3-PHENYL-3H-INDOLE-3-OLS

This invention relates to indole derivatives. More particularly it relates to a process for the preparation of certain pyrimido [1,2-a]indoles and to certain novel intermediates useful in the process.

The present invention provides a process for the preparation of a pyrimido[1,2-a]indole derivative of the general formula (I)

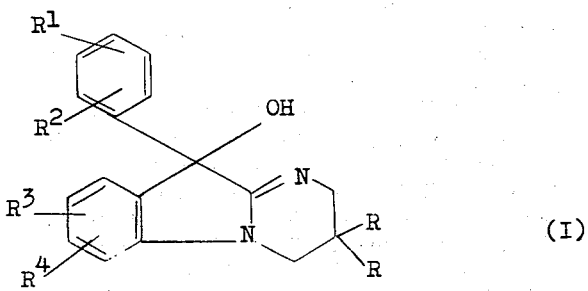

or an acid addition salt thereof, wherein R is hydrogen or lower alkyl (e.g. methyl), $R^1$, $R^2$, $R^3$ and $R^4$ are each hydrogen, hydroxyl, lower alkyl, lower alkoxy, trifluoromethyl or halogen which process comprises cyclising an indole derivative of the general formula (II)

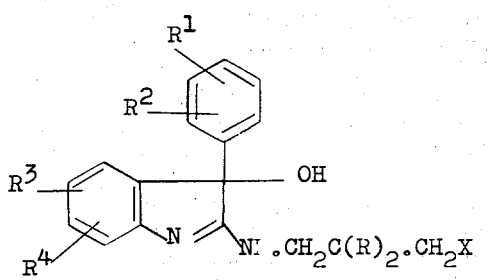

or an acid addition salt thereof, wherein R, $R^1$, $R^2$, $R^3$ and $R^4$ have the meanings given above and X is a halogen atom, preferably chlorine, and if desired converting a resulting free base into an acid addition salt.

The term "lower" as used herein means that the radical contains up to 6 carbon atoms, preferably up to 4 carbon atoms. Preferably R is hydrogen.

The following are examples of the groups $R^1$, $R^2$, $R^3$, $R^4$: hydrogen; hydroxyl; lower alklyl such as methyl, ethyl, propyl and butyl; lower alkoxy such as methoxy, ethoxy, propoxy and butoxy; trifluoromethyl and halogen such as fluorine, chlorine and bromine. Preferred meanings of $R^1$, $R^2$, $R^3$, $R^4$ are hydrogen and halogen.

A particularly preferred compound of general formula (I) is one in which $R^1$ is m-chloro and R, $R^2$, $R^3$ and $R^4$ are hydrogen.

The compound of general formula (II) in its free base form or as an acid addition salt thereof may be cyclised to the compound of general formula (I) by treatment with a base. A preferred base is an alkali metal alkoxide, e.g. sodium methoxide or ethoxide. The reaction may be carried out in an organic solvent which will dissolve the reactants but will not interfere with their interaction. The reaction mixture may be heated, for example at the reflux temperature, but heating is not generally necessary.

The product of general formula (I) is obtained in its free base form but it can be converted into its acid addition salts, e.g. the pharmaceutically acceptable acid addition salts by standard procedures. For example, the free base can be dissolved in a suitable organic solvent and the solution treated with a solution of the selected acid, in accordance with conventional procedures for preparing acid addition salts from base compounds. As examples of suitable acids, there may be used hydrochloric, hydrobromic, tartaric, phosphoric, maleic, citric, methanesulphonic or p-toluene sulphonic acids.

The indole compounds of general formula (II) and their acid addition salts are novel compounds and are provided by this invention.

Besides being useful as intermediates for preparing compounds of general formula (I), the compounds of general formula (II) and their pharmaceutically acceptable acid addition salts are also useful as anti-depressant agents. The compounds possess anti-depressant activity as shown for example by their activity in the reserpine hypothermia test (see Askew, Life Sciences, 1963, 1, 725–730) when administered to mice at dosages of between 3 and 100 mg/kg. Particularly preferred compounds having anti-depressant activity are 3-(m-chlorophenyl)-2-(3-chloropropylamino)-3H-indol-3-ol and its pharmaceutically acceptable acid addition salts. Some of the compounds of general formula (II), e.g., 2-(3-chloropropylamino)-3-phenyl-3H-indol-3-ol, also possess hypoglycaemic activity. The compounds of general formula (II) can be prepared by treating an alcohol of the general formula (III)

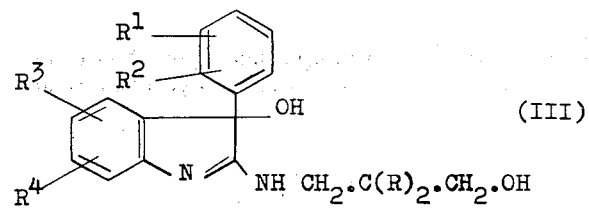

with a hydroxyl/halogen exchange reagent. By "a hydroxyl/halogen exchange reagent" is meant a reagent capable of displacing the hydroxyl group of an alcohol by a halogen atom. Typical examples are phosphorus trichloride, phosphoryl chloride and thionyl chloride. The preferred reagent is thionyl chloride. We have found that, surprisingly, use of such a reagent enables the hydroxyl group in the 2-substituent of the alcohol of general formula (III) to be displaced without displacing the hydroxyl group in the 3-position. The compound of general formula (II) can be isolated from the reaction medium by standard procedures. If the product is obtained as an acid addition salt, the free base can be obtained by basifying a solution of the acid addition salt. The free base can be converted into an acid addition salt, particularly a pharmaceutically acceptable acid addition salt by standard procedures, as described above in connection with the product of general formula (I). If desired compound (III) can be converted to compound (I), by the methods described above, without isolating the intermediate of general formula (II).

The starting material of general formula (III) can be prepared by a method similar to that described by Meyer et al., J. Org. Chem., 1968, 33, 4274. In this method an oxindole of general formula (IV)

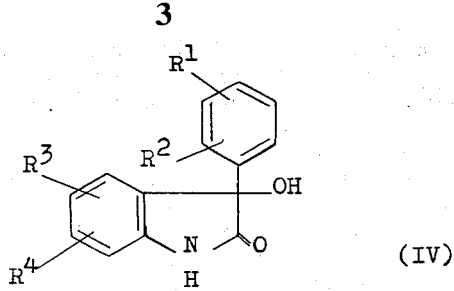

(IV)

wherein $R^1$, $R^2$, $R^3$ and $R^4$ have the meanings given above, is condensed with 3-amino-2,2-di(lower alkyl)-1-propanol or 3-aminopropanol. Preferably the reaction takes place in presence of a catalytic amount of p-toluene sulphonic acid and the water formed in the reaction is continuously removed. The reaction may take place in an organic solvent, such as xylene, preferably at the reflux temperature.

The oxindoles of general formula (IV) are known compounds or they may be prepared by known methods. For example isatin or a substituted isatin of the general formula (V)

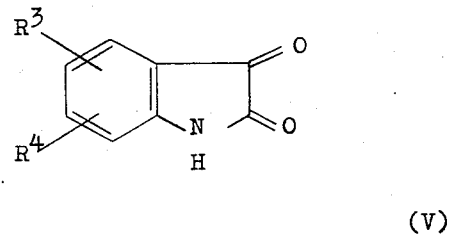

(V)

wherein $R^3$ and $R^4$ have the meanings given above may be reacted with a Grignard reagent of general formula (VI)

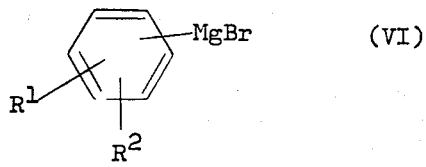

(VI)

wherein $R^1$ and $R^2$ have the meaning given above, for example, by the procedure given in Baumgarten et al., J. Amer. Chem. Soc., 1960, 82, 4634.

It will be appreciated that some of the compounds referred to above can exist in alternative tautomeric forms. Where in this specification there is used a name or formula implying a tautomer of particular structure it is to be understood that the name or formula includes any alternative tautomeric structures and mixtures of the tautomeric forms.

The compounds of general formula (I) are described in co-pending application Ser. No. 361,701 filed May 18, 1973 by Alan C. White under the title "10,10-Disubstituted 2,3,4,10-tetrahydro and 1,2,3,4,10,10a-hexahydropyrimido[1,2,-a]indole derivatives". Ser. No. 361,701 is a continuation-in-part of Serial No. 211,105 now abandoned filed Dec. 22, 1971 by Alan C. White.

The compounds of formulae (I) and (II) possess an asymmetric carbon atom and hence optical enantiomorphs are possible and the compounds may be obtained as the pure enantiomorphs or mixtures of such enantiomorphs, such as the racemates. The pure enantiomorphs may be obtained by the process of the present invention by employing optically active starting materials. Alternatively, a racemic mixture of the compound of general formula (I) or (II) may be resolved. A process for resolving a compound of formula (I) is described in U.S. Ser. No. 361,761 referred to above.

The compounds of general formula (I) exhibit inter alia anti-depressant activity, as described in U.S. Ser. No. 361,701 referred to above. Examples of specific compounds having good anti-depressant activity when tested by standard pharmacological tests include 2,3,4,10-tetrahydro-10-phenylpyrimido[1,2-a]indol-10-ol, and 10-(m-chlorophenyl)-2,3,4,10-tetrahydropyrimido[1,2-a]indol-10-ol.

As mentioned above the compounds of general formula (II) and their pharmaceutically acceptable acid addition salts exhibit pharmacological activity. Accordingly the invention further provides a pharmaceutical composition which comprises a compound of formula (II) or a pharmaceutically acceptable acid addition salt thereof, in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from 5 mg. or less to 500 mg. or more, according to the particular need and the activity of the active ingredient. The invention also includes the compounds in the absence of carrier where the compounds are in unit dosage form.

The following Examples illustrate the invention and the preparation of starting materials.

EXAMPLE 1

3-(m-Chlorophenyl)-2-(3-hydroxypropylamino)-3H-indol-3-ol 3-(m-Chlorophenyl)-3-hydroxy-3H-indol-2-one (25.9 g., U.K. specification No. 1,125,671), xylene (400 ml.), 3-aminopropanol (15 g.) and toluene-p-sulphonic acid (150 mg.) were heated under reflux, with stirring, in an apparatus fitted with a water separator. After 24 hours, 6.9 ml. of water and 3-aminopropanol had been collected. The mixture was cooled and the xylene removed under reduced pressure leaving a yellow crystalline material which was recrystallised from ethyl acetate to give the title compound (14.33 g.), m.p. 164° to 165°C. (Found C, 64.45; H, 5.4; N, 8.85. $C_{17}H_{17}Cl_2N_2O_2$ requires C, 64.75; H, 5.6; N, 8.7%).

EXAMPLE 2

3-(m-Chlorophenyl)-2-(3-chloropropylamino)-3H-indol-3-ol

Thionylchloride (2.2 g., 1.36 ml.) was added dropwise to a stirred suspension of 3-(m-chlorophenyl)-2-(3-hydroxypropylamino)-3H-indol-3-ol (3.16 g.) in chloroform (25ml.) at 0°C. The reaction mixture was heated under reflux for 45 minutes. the mixture was then cooled and the chloroform evaporated off at reduced pressure. Toluene (25 ml.) was added to the residue and after evaporation the procedure was repeated with a second quantity of toluene. The residue was then dissolved in the minimum quantity of isopropyl alcohol and a small quantity of ether was added to give the title compound as the hydrochloride, colourless rhombs (2.20 g.), m.p. 199° to 203°C.(decomp.). (Found C, 55.15; H, 4.6; N, 7.5. $C_{17}H_{16}N_2Cl_2O_2$ HCl requires C, 54.9; H, 4.6; N, 7.5%)

EXAMPLE 3

10-(m-Chlorophenyl)-2,3,4,10-tetrahydropyrimido[1,2-a]indol-10-ol 3-(m-Chlorophenyl)-2-(3-chloropropylamino)-3H-indol-3-ol hydrochloride (0.742 g.) was dissolved in methanol (10 ml.) containing sodium methoxide (0.27 g.) and left at room temperature for 64 hours. The solution was evaporated to a foam which was triturated with water. The product was isolated as a white powder (546 mg.), m.p. 186°–187°C. Recrystallisation from acetonitrile raised the melting point to 190°–192°C.

EXAMPLE 4

2-(3-Hydroxypropylamino)-3-phenyl-3H-indol-3-ol

3-Phenyl-3-hydroxy-3H-indol-2-one (4.5 g.) was heated under reflux with 3-aminopropanol (6.0 g.) in xylene (100 ml.) and toluene-p-sulphonic acid (150 mg) in an apparatus fitted with a water separator. After 24 hours the reaction mixture was cooled. The product crystallised and was filtered off and recrystallised from methanol to give the title compound, 3.81 g., m.p. 215°–217°C. (Found C, 72.4; H, 6.7; N. 9.9, $C_{17}H_{18}N_2O_2$ requires C, 72.3; H, 6.4; N, 9.9%).

EXAMPLE 5

2-(3-Chloropropylamino)-3-phenyl-3H-indol-3-ol

Thionylchloride (1.53 ml.) was added dropwise to a stirred cooled suspension of 2-(3-hydroxypropylamino)-3-phenyl-3H-indol-3-ol (3 g.) in chloroform (25 ml.). On completion of the addition the reaction was allowed to warm to room temperature and then heated under reflux for 45 minutes. The solvent and excess thionyl chloride were removed under reduced pressure and the resulting product crystallised from isopropanol-ether to give the title compound as its hydrochloride salt (2.72 g.). After two recrystallisations from isopropanol-ether the hydrochloride had a m.p. 210°–212°C. (Found C, 60.8; H. 5.6; N, 8.3. $C_{17}H_{17}ClN_{20}$ HCl requires C, 60.5; H, 5.4; N 8.3%).

EXAMPLE 6

Cyclisation of 2-(3-chloropropylamino)-3-phenyl-3H-indol-3-ol with sodium methoxide by a process analogous to that described in Example 3 gives 2,3,4,10-tetrahydro-10-phenylpyrimido[1,2-a]indol-10-ol.

EXAMPLE 7 a. Reaction of 3-aminopropanol with 5-chloro-3-hydroxy-3-phenyl-3H-indol-2-one in presence of toluene-p-sulphonic acid by a procedure analogous to that of Example 1 gives 5-chloro-2-(3-hydroxypropylamino)-3-phenyl-3H-indol-3-ol.

b. Reaction of 5-chloro-2-(3-hydroxypropylamino)-3-phenyl-3H-indol-3-ol with thionylchloride by a procedure analogous to that described in Example 2 gives 5-chloro-2-(3-chloropropylamino)-3-phenyl-3H-indol-3-ol.

c. Cyclisation of 5-chloro-2-(3-chloropropylamino)-3-phenyl-3H-indol-3-ol with sodium methoxide by a process analogous to that of Example 3 gives 8-chloro-2,3,4,10-tetrahydro-10-phenylpyrimido[1,2-a]indol-10-ol.

EXAMPLE 8 a. Reaction of 3-aminopropanol with 3-hydroxy-3-(m-tolyl)-3H-indol-2-one in presence of toluene-p-sulphonic acid by a procedure analogous to that of Example 1 gives 2-(3-hydroxypropylamino)-3-(m-tolyl)-3H-indol-3-ol.

b. Reaction of 2-(3-hydroxypropylamino)-3-(m-tolyl-3H-indol-3-ol with thionylchloride by a procedure analogous to that described in Example 2 gives 2-(3-chloropropylamino)-3-(m-tolyl)-3H-indol-3-ol.

c. Cyclisation of 2-(3-chloropropylamino)-3-(m-tolyl)-3H-indol-3-ol with sodium methoxide by a process analogous to that of Example 3 gives 2,3,4,10-tetrahydro-10-(m-tolyl)-pyrimido[1,2-a]indol-10-ol.

EXAMPLE 9 a. Reaction of 3-aminopropanol with 3-(m-fluorophenyl)-3-hydroxy-3H-indol-2-one in presence of toluene-p-sulphonic acid by a procedure analogous to that of Example 1 gives 3-(m-fluorophenyl)-2-(3-hydroxypropylamino)-3H-indol-3-ol.

b. Reaction of 3-(m-fluorophenyl-2-(3-hydroxypropylamino)-3H-indol-3-ol with thionylchloride by a procedure analogous to that described in Example 2 gives 3-(m-fluorophenyl)-2-(3-chloropropylamino)-3H-indol-3-ol.

c. Cyclisation of 3-(m-fluorophenyl)-2-(3-chloropropylamino)-3H-indol-3-ol with sodium methoxide by a process analogous to that of Example 3 gives 10-(m-fluorophenyl)-2,3,4,10-tetrahydropyrimido[1,2-a]indol-10-ol.

EXAMPLE 10 a. Reaction of 3-aminopropanol with 3-(3,4-dichlorophenyl)-3-hydroxy-3H-indol-2-one in presence of toluene-p-sulphonic acid by a procedure analogous to that of Example 1 gives 3-(3,4-dichlorophenyl)-2-(3-hydroxypropylamino)-3H-indol-3-ol b. Reaction of 3-(3,4-dichlorophenyl)-2-(3-hydroxypropylamino)-3H-indol-3-ol with thionylchloride by a procedure analogous to that described in Example 2 gives 3-(3,4-dichlorophenyl-2-(3-chloropropylamino)-3H-indol-3-ol.

c. Cyclisation of 3-(3,4-dichlorophenyl)-2-(3-chloropropylamino)-3H-indol-3-ol with sodium methoxide by a process analogous to that of Example 3 gives 10-(3,4-dichlorophenyl)-2,3,4,10-tetrahydropyrimido[1,2-a]indol-10-ol.

EXAMPLE 11 a. Reaction of 3-aminopropanol with 3-(m-anisyl)-3-hydroxy-3H-indol-2-one in presence of toluene-p-sulphonic acid by a procedure analogous to that of Example 1 gives 3-(m-anisyl)-3-(3-hydroxypropylamino)-3H-indol-3-ol.

b. Reaction of 3-(m-anisyl)-2-(3-hydroxypropylamino)-3H-indol-3-ol with thionylchloride by a procedure analogous to that described in Example 2 gives 3-(m-anisyl)-2-(3-chloropropylamino)-3H-indol-3-ol.

c. Cyclisation of 3-(m-anisyl)-2-(3-chloropropylamino)-3H-indol-3-ol with sodium methoxide by a process analogous to that of Example 3 gives 10-(m-anisyl)-2,3,4,10-tetrahydropyrimido[1,2-a]indol-10-ol.

EXAMPLE 12 a. Reaction of 3-aminopropanol with 3-hydroxy-(3-(m-trifluoromethylphenyl)-)-3H-indol-2-one in presence of toluene-p-sulphonic acid by a procedure analogous to that of Example 1 gives 2-(3-hydroxypropylamino)-3-(m-trifluoromethylphenyl)-3H-indol-3-ol.

b. Reaction of 5-chloro-2-(3-hydroxypropylamino)-3-phenyl-3H-indol-3-ol with thionylchloride by a procedure analogous to that described in Example 2 gives 2-(3-chloropropylamino)-3-(m-trifluoromethylphenyl)-3H-indol-3-ol.

c. Cyclisation of 2-(3-chloropropylamino)-3-(m-trifluoromethylphenyl)-3H-indol-3-ol with sodium methoxide by a process analogous to that of Example 3 gives 2,3,4,10-tetrahydro-10-(m-trifluoromethylphenyl)-pyrimido[1,2-a]indol-10-ol.

I claim:

1. A compound selected from the group consisting of indole derivatives of formula (II)

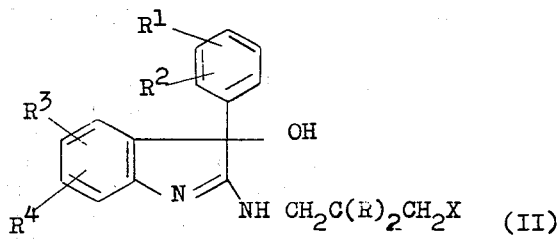

and the pharmaceutically acceptable acid addition salts thereof, wherein R is hydrogen or lower alkyl, each $R^1$, $R^2$, $R^3$ and $R^4$ is independently selected from the group consisting of hydrogen, hydroxyl, lower alkyl, lower alkoxy, trifluoromethyl and halogen and X is a halogen atom.

2. A compound as defined in claim 1 wherein X is chlorine and $R^1$, $R^2$ $R^3$ and $R^4$ are each hydrogen or halogen, and R is hydrogen.

3. A compound as defined in claim 1 which is 3-(m-chlorophenyl)-2-(3-chloropropylamino)-3H-indol-3-ol or a pharmaceutically acceptable acid addition salt thereof.

4. A compound as defined in claim 1 which is 2-(3-chloropropylamino)-3-phenyl-3H-indol-3-ol or a pharmaceutically acceptable acid addition salt thereof.

* * * * *